United States Patent [19]

Kitzing et al.

[11] 4,043,995
[45] Aug. 23, 1977

[54] PROCESS FOR CROSSLINKING HYDROPHILIC COLLOIDS

[75] Inventors: Rainer Kitzing; Norman Alfred Smith, both of Ilford, England

[73] Assignee: Ciba-Geigy AG, Basel, Switzerland

[21] Appl. No.: 578,585

[22] Filed: May 19, 1975

[30] Foreign Application Priority Data

June 5, 1974 United Kingdom ............... 24888/74
Oct. 25, 1974 United Kingdom ............... 46165/74

[51] Int. Cl.² .............................................. C09H 7/00
[52] U.S. Cl. .................................... 260/117; 96/111; 526/9; 544/180; 544/190; 544/194; 544/204; 544/195; 544/199

[58] Field of Search ................ 260/117, 246 B, 249.8; 526/9; 96/111

[56] References Cited

U.S. PATENT DOCUMENTS

| 3,645,743 | 2/1972 | Mucke | 96/111 |
| 3,826,788 | 7/1974 | Froehlich | 96/111 |

Primary Examiner—Paul R. Michl
Attorney, Agent, or Firm—Burgess, Dinklage & Sprung

[57] ABSTRACT

The present invention relates to a process for crosslinking hydrophilic colloids, preferably gelatine and most preferably gelatine present in a photographic material. A 1,3,5-triazine compound containing an NC—N⁻— substituent bound to the triazine ring is incorporated into the hydrophilic colloid as a crosslinking agent.

12 Claims, No Drawings

PROCESS FOR CROSSLINKING HYDROPHILIC COLLOIDS

The use of triazine compounds as crosslinking agents for hydrophilic colloids and in particular gelatin is known from the German Auslegeschrift No. 1,284,290. In German Offenlegungsschrift No. 1,547,750 there are described other triazine compounds which function as crosslinking agents for hydrophilic compounds. The triazine compounds of the DT-OS have bonded to the s-triazine ring a removable onium group which increases the water solubility of the triazine compounds.

It is the object of the present invention to provide a process for crosslinking hydrophilic colloids using other substituted triazine compounds.

According to the present invention there is provided a process for crosslinking hydrophilic colloids which contain amino, imino and/or hydroxyl groups, which comprises incorporating into the hydrophilic colloid as a crosslinking agent a compound of the formula

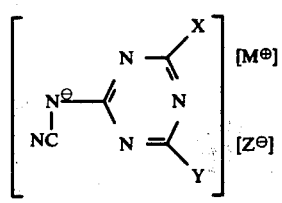

(1)

wherein each of X and Y are a fluorine, chlorine or bromine atom or a hydroxy group, a lower alkoxy group or a radical of the formula

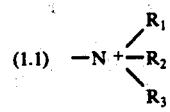

(1.1)

wherein $R_1$, $R_2$ and $R_3$ are each optionally substituted alkyl, alkenyl, alkinyl, cycloalkyl, aryl, aralkyl or together with the nitrogen atom to which they are bonded form a saturated or unsaturated ring which optionally contains yet other heteroatoms, and M is a cation and Z is an anion, one of which or neither may be required to balance the charge in the triazine ring system.

By lower alkoxy group is meant an alkoxy group wherein the alkyl moiety contains from 1–6 carbon atoms.

The cation $M^+$ may be for example a hydrogen ion or a lithium, sodium, potassium, rubidium, caesium, magnesium or calcium ion or it may be an ammonium or substituted ammonium ion. However preferably M is a sodium ion. $Z^-$ may be an anion for example chloride, iodide, perchlorate, fluorborate, hexafluarsenate or hexafluorphosphate. The anion when present has no effect on the hardening properties of the triazine but effects the water solubility of the compound.

Examples of substituents which may be present in $R_1$, $R_2$ and/or $R_3$ are halogen atoms, nitro, amino or carbonyl groups. When $R_1$, $R_2$, $R_3$ are cycloalkyl, aryl or aralkyl these rings may be substituted by alkyl groups containing 1–4 carbon atoms.

Examples of saturated or unsaturated rings which $R_1$, $R_2$ and $R_3$ may form together with the nitrogen to which they are bonded are unsubstituted or alkyl-substituted morpholinium, thiomorpholinium, pyrrolidinium, piperidinium and pyridinium radicals, wherein the alkyl substituents contain 1 to 5, preferably 1 to 3, carbon atoms, and the radical of the formula

(1.2)

The preferred compounds of use in the invention are those wherein both X and Y are chlorine atoms. Other compounds of particular interest are those wherein one of X and Y is a chlorine atom and the other a radical of formula (1.1) and compounds wherein both X and Y are a radical of formula (1.1).

Particularly preferred compounds are those of the formulae (2) to (6) which follow:

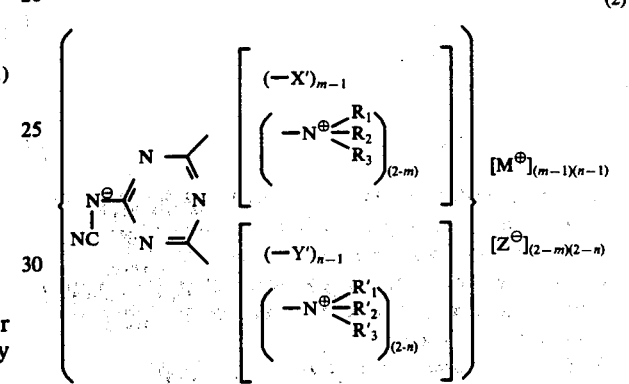

(2)

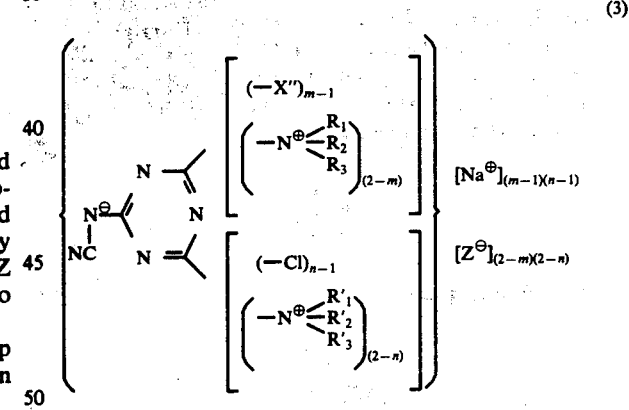

(3)

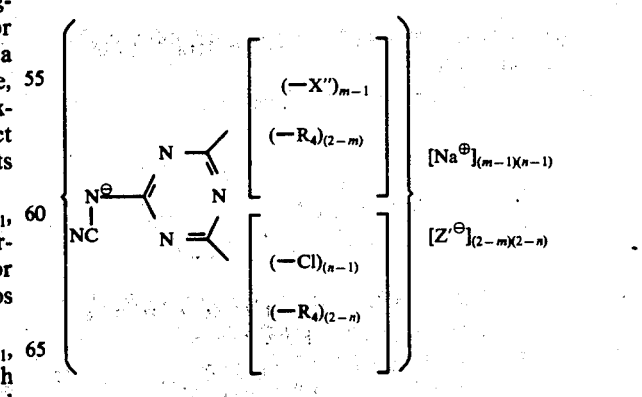

(4)

(5)

-continued

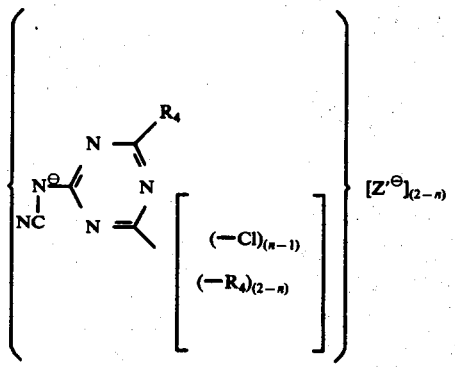

(6)

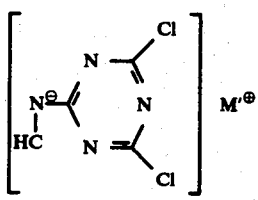

In the formulae the individual symbols throughout have the same meaning and denote the following:

M — same meaning as in formula (1), see above;
M' — hydrogen, lithium sodium, potassium, rubidium, caesium, magnesium, calcium or optionally substituted ammonium ion;
$R_1, R_2, R_3$ — same meaning as in formula (1),
$R_1', R_2', R_3'$ — also each denote optionally substituted alkyl, alkenyl, alkinyl, cycloalkyl, aryl aralkyl or together with the nitrogen atom to which they are bonded form a ring which optionally contains yet other hetero atoms, e.g. a second nitrogen or an oxygen atom. If a group

as well as a group

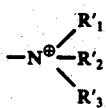

is present in the molecule they are preferably of the same constitution;
$R_4$ — one of the radicals of the formulae

X',Y' — a fluorine, chlorine or bromine atom or a hydroxy group or a lower alkoxy group;
X'' — chlorine atom or a hydroxy group;
Z — same meaning as in formula (1), see above;
Z' — a chloride, iodide, perchlorate, fluoborate, hexafluoarsenate or hexafluorphosphate ion;
m, n — same meaning as in formula (1), each is 1 or 2, impendently from one another.

Compounds of formula (1) wherein X and Y are other than a radical of formula (1.1) may be prepared by reacting a cyanuric compound of the formula

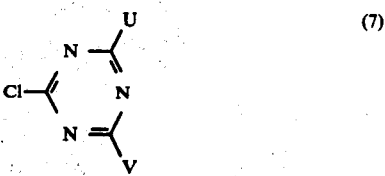

(7)

wherein U and V are each a fluorine, chlorine or bromine atom with at least an equal molar quantity of a cyanamide salt in aqueous solution at a temperature of 0°-10° C.

The compounds of formula (1) wherein either X or Y or both X and Y are a radical for formula (1.1) are novel compounds and thus represent a special feature of the present invention. They correspond to the formula (8)

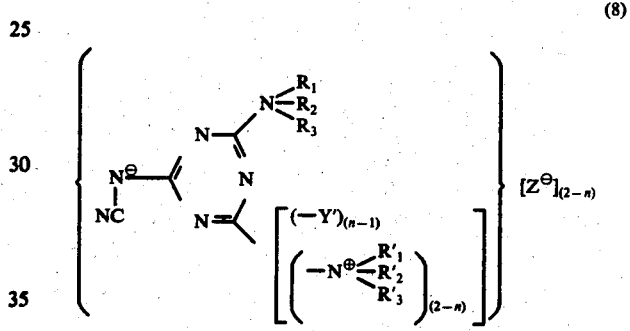

The preferred new triazine compounds correspond to the formula (9)

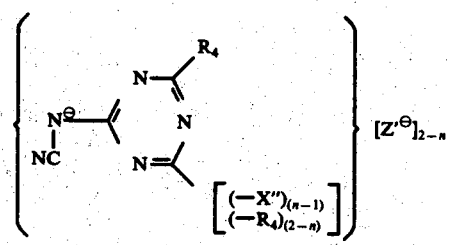

Compounds of formula (1) wherein one of X and Y is a radical of formula (1.1) are advantageously prepared from a compound of the formula (10)

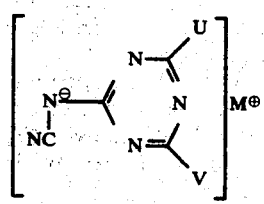

wherein U and V are each a chlorine, fluorine or bromine atom, by dissolving a quantity of a compound of formula (10) in water and then adding an equal molar quantity of tertiary amine, with stirring, at room temperature to produce a compound of the formula

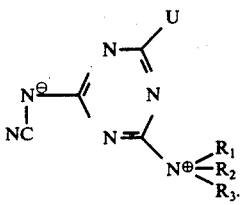
(11)

Compounds of formula (1) wherein each of X and Y are a radical of formula (1.1) may be prepared from a compound of formula (10) by dissolving a quantity of a compound of formula (20) in water and then adding a greater than 2 molar quantity of the appropriate tertiary amine, with stirring at room temperature adding a salt and then cooling the mixture, to produce a compound of formula

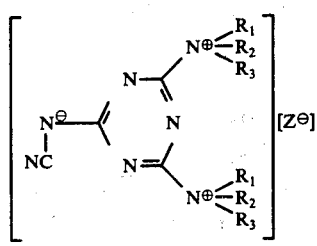
(12)

wherein Z is an anion.

The compounds of formula (1) wherein neither X nor Y are a radical of formulae (1.1) require a cation M.

The compounds of formula (11) are zwitterionic and require neither a cation M nor an anion Z.

The compounds of formula (12) require an anion Z.

Preferably in the reactions to produce compounds of formula (11) and (12) the compounds of formula (10) employed is the sodium salt of 2-cyanoamino-4,6-dichlorotriazine.

Examples of tertiary amines which may be employed are trialkyl amines, for example trimethylamine, dialkylcyclohexylamine, dialkylpropinyl amine, N-alkylmorpholine N-alkylpyrrolidine, N-alkylpiperidine, pyridine and the compound

The crosslinking process of the present invention can be used in the textile and leather industry, the manufacture of paper and the plastics, glue and gelatin industry. Above all, it can be used as a process for hardening water-soluble colloids for example polyvinyl alcohol, gelatin or gelatin derivatives, especially when these colloids are in the form of layers of photographic materials. The reaction of these colloids with the triazine compounds of use in the present invention in general takes place easily, and in the usual manner. The triazine compounds are, as a rule, sufficiently water-soluble to be used as aqueous solutions.

In most cases in order to carry out the process of the present invention it suffices to add the triazine compounds of use in the present invention as an aqueous solution or in a solid form which is a finely divided as possible, to an aqueous solution of the hydrophilic colloid, with good stirring.

Thus, a solution of the triazine crosslinking agent in water, or mixed with, for example, ethanol, methanol or acetone, can be brought together with the colloids at normal or slightly raised temperature. Gelatin, which optionally may contain silver halide and/or other components required to produce photographic images, has proved particularly suitable for crosslinking by the process of the present invention.

The coating solution which is an aqueous solution containing both gelatin and the triazine cross-linking agent can, in the usual way, be coated on a substrate to form a layer, and be dried. The layer can then be left at raised temperature or at room temperature for a certain time, for example up to 24 hours. Thereupon cross-linking, which is evidenced by hardening of the layer, takes place rapidly and progressively; the melting point of the gelatin is raised substantially, for example from 25° to 60° C, and the reciprocal swelling factor increases correspondingly.

The amount of the triazine cross-linking agent used depends on the desired degree of hardening of the gelatin layer required but is suitably from 0.1 to 10 per cent by weight based on the weight of the dry gelatin.

A particular advantage of the process of the present invention is that when the triazine cross-linking agents are used at a low concentration they impart a sufficient degree of hardness to the gelatin layers in 18 to 24 hours, so that the coated material can be tested by processing a sample immediately following its manufacture, even if the test be carried out at a raised temperature or in strong processing baths.

It is a further advantage that during the process of the present invention, no significant change in pH of the gelatin layer occurs.

The cross-linking or hardening effect itself is very stable; even after prolonged storage at temperatures around 40° C and at a relative atmospheric humidity of about 70%, the reciprocal swelling factor remains above 0.2 (compare Table 1).

Further the degree of hardening is also not changed significantly by acids or bases even on prolonged action, which indicates that the hardener-gelatin bond created has great resistance to hydrolysis.

The triazine compounds of use in the present invention are furthermore generally sufficiently soluble in water and sufficiently stable in aqueous solutions to enable the process of the present invention to be used in the preparation of photographic material. Thus, for example, it is particularly desirable — for the continuous manufacture of photographic materials — that batches of solutions of cross-linking agents should remain stable at room temperature for several hours or days and that its concentration should not decrease or should only do so insignificantly. Also it is important that in the coating solution, at about 40° C, the hardener should undergo very little or no decomposition and very little or no reaction with water during the requisite standing time and dwell time, so as to maintain its full crosslinking action over the course of several hours, during coating, drying and storage of the photographic material.

Furthermore, the viscosity of the coating solution should not significantly increase during the standing time as a result of the addition of the hardener. It is also particularly important that even on prolonged treatment of the coated layer at raised temperature and atmospheric humidity conditions the hardener should not cause any yellowing, fogging of photographic material or effect on the graduation of the material on development.

The compounds of use in the process of the present invention fulfil the above desiderata very well. In particular they hydrolyse very little when present in an aqueous solution. They do not discolour gelatin. When these compounds are added to a gelatin solution they cause only a small increase in the viscosity of the solution and thus such solutions can be coated without difficulty. The compounds have a good hardening effect over a wide pH range and thus can be used in the preparation of a wide range of photographic materials. Furthermore the compounds are easy to produce in high yield and the starting material, usually cyanuric chloride, is cheap.

Thus the process of the present invention is suitable for hardening (cross-linking) all the layers in photographic material containing gelatin for example, intermediate layers, emulsion layers, base layers, top layers, backing layers and anti-halation layers. The layers can contain not only the crosslinking agents but also additives of the most diverse knife for example, silver halide, pigments, such as barium sulphate, titanium dioxide or silicon dioxide or those of organic nature, such as coloured pigments, and also image dyestuffs, colour coupling agents, latices, sensitisers, filter dyestuffs, antihalation dyestuffs and light screening dyestuffs, emulsion stabilisers, UV absorbers, optical brighteners and even other crosslinking agents.

In the following a prescription is given for the preparation of Na salt of 2-cyanoamino-4,6-dichlorotriazine which can be used itself as a hardener and which will be used as a starting material in several Examples.

27 ml of 25 % aq cyanamide solution is added dropwise to a stirred mixture of 29.6 g cyanuric chloride in 160 g ice and 16 ml acetone at 0°–5° C; pH8–9 is maintained by addition of NaOH solution. The resulting mixture is left overnight at 0° then dissolved by the minimum addition of water (20°–25° C). The solution is filtered and the product precipitated by adding NaCl. The product is filtered, washed with cold water and dried.

Yield 31 g

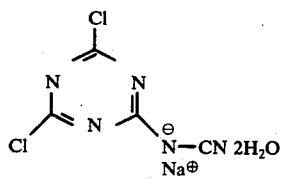

This compound is hereinafter referred to as Hardener 1.

EXAMPLE 1

Preparation of Hardener 2

4.96 g (0.02 moles) of the sodium salt of 2 cyanoamino-4,6-dichlorotriazine as prepared above is disolved in 75 ml water and then 1.98 g (0.02 moles) of N-methylpiperidine is added dropwise with stirring at 18°–20° C. After ½ hours the solid precipitate obtained is filtered, washed with water and dried.

Yield 4.0 g

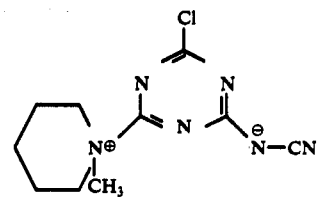

Hardener 2.

EXAMPLE 2

Preparation of Hardener 3

4.96 g (0.02 moles) of the sodium salt of 2 cyanoamino-4.6-dichlorotriazine is dissolved in 75 ml of water and 4.95 g (0.05 moles) N-methylpiperidine is added dropwise at 15°–20° C. After 2 hours the solution is filtered and the filtrate is treated with 10 g Na $ClO_4$, dissolved in water and then left for 2 hours on ice. The precipitate is collected, washed with water and then recrystallised from water.

Yield 1.6 g

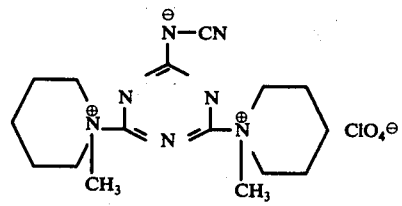

Hardener 3.

EXAMPLE 3

Hardener 4

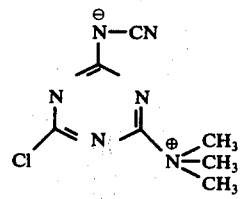

is prepared analogously to hardener 2 following the method described in Example 1 using 0.02 moles of trimethylamine dissolved in water. Yield 1.6 g.

EXAMPLE 4

Hardener 5

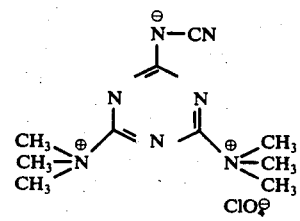

is prepared analogously to hardener 3 following the method described in Example 2 using 0.05 moles of trimethylamine dissolved in water. Yield 1.7 g.

EXAMPLE 5

Hardener 6

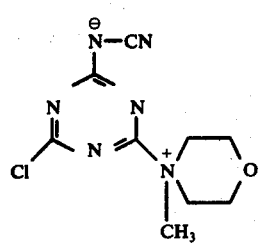

is prepared analogously to hardener 2 following the method described in Example 1 using 0.02 moles of N-methylmorpholine. Yield 4.2 g.

EXAMPLE 6

Hardener 7

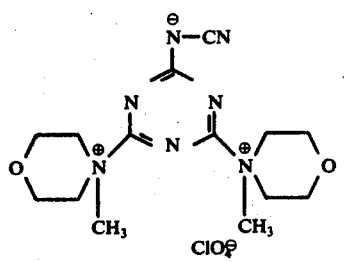

is prepared analogously to hardener 3 following the method described in Example 2 using 0.05 moles of N-methylmorpholine. Yield 1.2 g.

EXAMPLE 7

Hardener 8

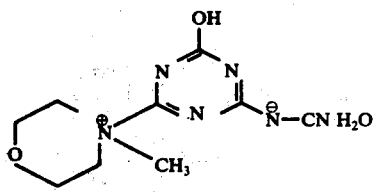

4.1 g (0.01 Moles) of Hardener 7 is dissolved in 65 ml hot water and the solution kept at 70°-80° C for 1 hour. After cooling in ice the product is filtered, washed cold water and then dried. Yield 1.8 g.

EXAMPLE 8

Hardener 9

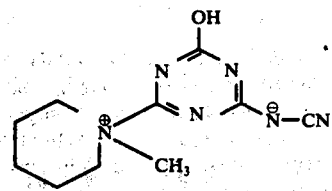

is prepared analogously to Hardener 8 in Example 7 using 0.01 mole of hardener 3 and heating for 2½ hour. at 70°-80°. Yield 1.5 g.

EXAMPLE 9

Hardener 10

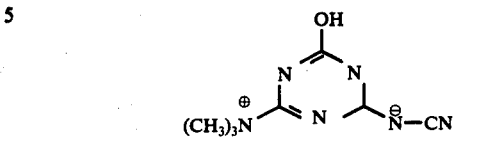

is prepared analogously to Hardener 8 in Example 7 using 0.01 mole of hardener 5 and heating at 70°-80° for 30 minutes. Yield 0.9 g.

EXAMPLE 10

Hardener 11

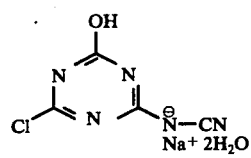

2.48 g (0.01 mole) of Hardener 1 is added with stirring to a solution of 1.2 g (0.03 mole) of sodium hydroxide in 20 ml water at 20°-25° C. Slight cooling is required to keep the temperature at 20°-25° C. After ½ hour the solid which has precipitated is dissolved by adding 25 ml water. The solution is then adjusted to pH7 with concentrated HCl. The mixture is then cooled in ice, the precipitate filtered, washed with cold water and dried. Yield 2.0 g.

EXAMPLE 11

In the Example which follows, the reciprocal swelling factor is used as a measure of the hardening. The samples were prepared as follows:

6 ml of a 6% strength gelatine solution, 1 ml of a 1% strength dyestuff solution of the formula

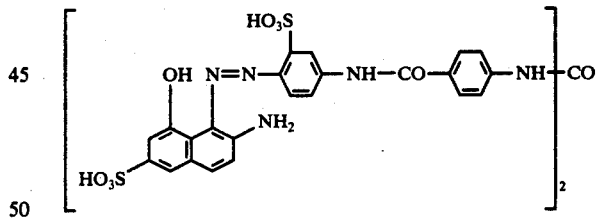

1 ml of a $25.10^{-3}$ molar solution of hardener 1 and 5 ml of deionised water are mixed and the pH adjusted to 6.5. The solution is coated on a 13 x 18 cm triacetate film. After solidification at 10° C, the layer is dried over the course of 1 hour at approx. 20° C. (The dyestuff merely serves to make the samples more readily visible during the swelling measurements.) Some samples of the coated film were stored under room conditions (NK, approx. 20° C, 50% relative atmospheric humidity) and other samples were incubatesd (CL, 43° C, 69% relative atmospheric humidity).

To determine the reciprocal swelling factor, a thin section of approx. 20 μ is prepared from each of the samples and measured under a microscope. The thickness of the dry gelatin layer is then determined, deionised water is then added and after 4 minutes the thickness of the swollen gelatin layer is measured. The reciprocal swelling factor 1/SF corresponds to the following ratio:

$$1/SF = \frac{\text{Thickness of the dry layer}}{\text{Thickness of the swollen layer}}$$

The results obtained were as follows:

TABLE I

| Hardener | Concentration mM/100g GEL | N.K. 1/SF after | | | | C.L. 1/SF after | | |
|---|---|---|---|---|---|---|---|---|
| | | 3 hours | 2 days | 7 days | 14 days | 2 days | 7 days | 14 days |
| 1 | 3.5 | 0.100 | 0.113 | 0.147 | 0.149 | 0.226 | 0.286 | 0.275 |
| 1 | 7 | 0.102 | 0.132 | 0.179 | 0.194 | 0.280 | 0.339 | 0.364 |
| 2 | 7 | 0.129 | 0.208 | 0.221 | | 0.263 | 0.246 | |
| 3 | 3.5 | 0.193 | 0.187 | 0.211 | 0.208 | 0.278 | 0.296 | 0.296 |
| 4 | 7 | 0.197 | 0.254 | 0.236 | 0.246 | 0.333 | 0.313 | 0.304 |
| 5 | 3.5 | 0.123 | 0.186 | 0.179 | 0.188 | 0.236 | 0.233 | 0.241 |
| 6 | 7 | 0.113 | 0.133 | 0.118 | | 0.175 | 0.200 | |
| 7 | 3.5 | 0.140 | 0.174 | 0.179 | 0.189 | 0.264 | 0.264 | 0.275 |
| 8 | 7 | 0.159 | 0.204 | 0.225 | | 0.289 | 0.340 | |
| 9 | 7 | 0.109 | 0.120 | 0.175 | | 0.304 | 0.356 | |
| 10 | 7 | 0.140 | 0.182 | 0.208 | | 0.308 | 0.336 | |
| 11 | 7 | 0.095 | 0.133 | 0.180 | 0.213 | 0.198 | 0.220 | 0.243 |

EXAMPLE 12

Viscosity measurements are carried out on 10% strength aqueous gelatin solutions in a capillary viscometer of the Ostwald type at 40° C. The effect of hardener 1 on this gelatin solution at various pHs is measured. The comparison substance (A) which is used is the crosslinking agent of the formula

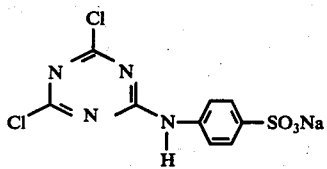

10.27 of deionised gelatin are swollen in 100 ml of distilled water for 30 minutes at room temperature and then stirred for 1 hour at 50° C. 30 ml of this solution are taken, 0.4 ml of an 8% strength solution of a wetting agent (the sodium salt of an alkylnaphthalene-sulphonic acid) is added and the pH is adjusted to the desired value of 6.5 by means of the requisite amount of 1 molar sodium hydroxide solution or hydrochloric acid solution.

0.2 mole of one of the above mentioned crosslinking agents is then dissolved in 10 ml of water and added to the above gelatin solution. The mixture is made up to a total volume of 57.1 ml with distilled water, 20 ml of this solution are withdrawn 5 minutes after the addition of the solution of the crosslinking agent and the viscosity of this solution is followed in a viscometer for 4 hours at 40° C.

The results are summarised in Table 2. They show that in the case of the crosslinking agents according to the invention the viscosity undergoes virtually no change or only an insignificant change. The comparison compound shows a sharp rise in the viscosities and hence an undesired change in the gelatin solution.

The viscosity figures shown are in centipoises.

TABLE 2

| Hardener used | pH | Viscosity after hours | | | |
|---|---|---|---|---|---|
| | | 0 | 1 | 2 | 3 |
| Hardener 1 | 4.5 | 19.64 | 20.29 | 21.11 | 21.95 |
| " | 5.5 | 21.36 | 22.06 | 22.76 | 23.62 |
| " | 6.5 | 22.73 | 23.23 | 23.77 | 24.36 |
| "7.5 | 22.76 | 23.79 | 23.79 | 24.24 | |

TABLE 2-continued

| Hardener used | pH | Viscosity after hours | | | |
|---|---|---|---|---|---|
| | | 0 | 1 | 2 | 3 |
| Comparative hardener A | 6.5 | 36.50 | 47.61 | 62.33 | |

What we claim is:

1. A process for crosslinking hydrophilic colloids which contain amino, imino and/or hydroxyl groups, which comprises incorporating into the hydrophilic colloid as a crosslinking agent a compound of the formula

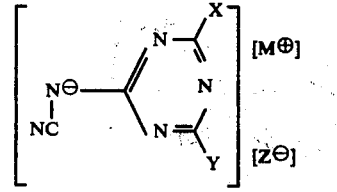

wherein each of X and Y are a fluorine, chlorine or bromine atom or a hydroxy group, a lower alkoxy group or a radical of the formula

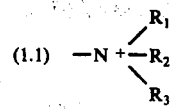

wherein $R_1$, $R_2$ and $R_3$ are each optionally substituted alkyl, alkenyl, alkinyl, cycloalkyl, aryl, aralkyl or together with the nitrogen atom to which they are bonded form a saturated or unsaturated ring which optionally contains yet other heteroatoms, and M is a cation and Z is an anion, one of which or neither may be required to balance the charge in the triazine ring system.

2. A process according to claim 1 which comprises employing as crosslinking agent a compound of the formula.

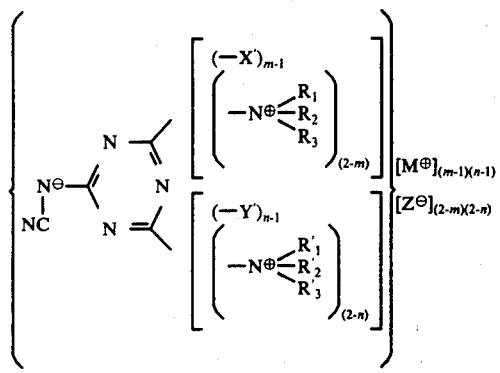

wherein X' and Y' each represent a fluorine, chlorine or bromine atom or a hydroxy group or a lower alkoxy group, $R_1$, $R_2$, $R_3$, $R'_1$, $R'_2$ and $R'_3$ represent optionally substituted alkyl, alkenyl, alkinyl, cycloalkyl, aryl, aralkyl or together with the nitrogen atom to which they are bonded form a ring which optionally contains yet other heteroatoms, M represents a cation and Z an anion and $m$ and $n$ each is 1 or 2.

3. A process according to claim 2 which comprises employing as a crosslinking agent a compound of the formula

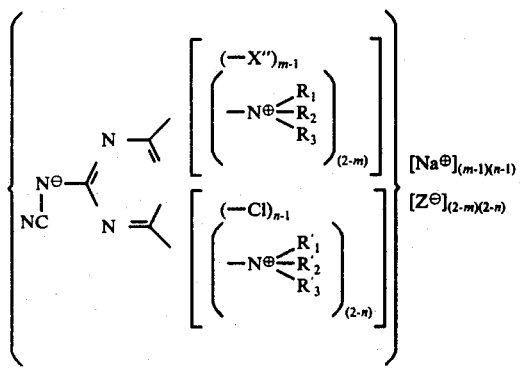

wherein X" represents a chlorine atom or a hydroxy group, Z' represents a chloride, iodide, perchlorate fluoroborate, hexafluoarsenate or hexafluorphosphate ion and $R_1$, $R_2$, $R_3$, $R'$, $R'_2$, $R'_3$, $m$ and $n$ have the meaning given in claim 2.

4. A process according to claim 3 which comprises employing as a crosslinking agent a compound of the formula

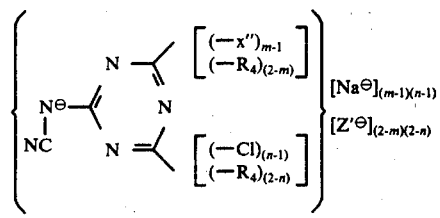

wherein —$R_4$ corresponds to one of the radicals of the formulae

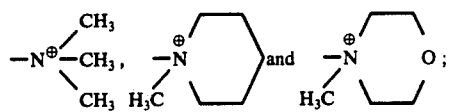

and X", Z', $m$ and $n$ have the meaning given in claims 2 and 3.

5. A process according to claim 4 which comprises employing as a crosslinking agent a compound of the formula

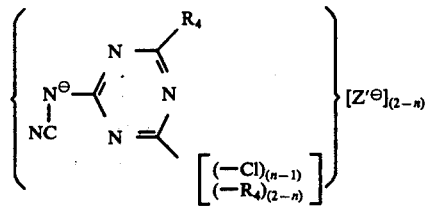

wherein $R_4$, Z', $m$ and $n$ have the meaning given in claims 2, 3 and 4.

6. A process according to claim 2 which comprises employing as a crosslinking agent a compound of the formula

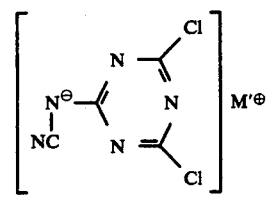

wherein M' represents a hydrogen, lithium, sodium potassium, rubidium, caesium, magnesium, calcium or ammonium ion.

7. A process according to claim 1 which comprises crosslinking polyvinyl alcohol, gelatin or a gelatin derivative.

8. A process according to claim 7 which comprises crosslinking the colloid in the form of a layer in photographic material or crosslinking the colloid and then forming a photographic material with the crosslinked colloid.

9. A process according to claim 7 which comprises crosslinking gelatin in the form of a gelatino silver halide emulsion.

10. A process according to claim 9 wherein the amount of the triazine cross-linking agent of the formula firstly set forth in claim 1 is from 0.1 to 10 per cent by weight on the weight of the dry gelatin in the layer.

11. A hardened gelatino silver halide emulsion layer in photographic material which has been cross-linked by the process claimed in any one of claims 8 to 10.

12. Photographic material which contains at least one layer as claimed in claim 11.

* * * * *

UNITED STATES PATENT AND TRADEMARK OFFICE
CERTIFICATE OF CORRECTION

PATENT NO. : 4,043,995
DATED : Aug. 23, 1977
INVENTOR(S) : Rainer Kitzing et al

It is certified that error appears in the above—identified patent and that said Letters Patent is hereby corrected as shown below:

Column 14, line 60, Delete "anyone of claims 8 to 10" and insert --claim 10 --.

Signed and Sealed this

Sixth Day of November 1984

[SEAL]

Attest:

GERALD J. MOSSINGHOFF

Attesting Officer

Commissioner of Patents and Trademarks